United States Patent [19]

Thomas, Jr.

[11] 4,444,760

[45] Apr. 24, 1984

[54] PURIFICATION AND CHARACTERIZATION OF A PROTEIN FIBROBLAST GROWTH FACTOR

[75] Inventor: Kenneth A. Thomas, Jr., Cranford, N.J.

[73] Assignee: Merck & Co., Inc., Rahway, N.J.

[21] Appl. No.: 505,553

[22] Filed: Jun. 17, 1983

[51] Int. Cl.$^3$ ..................... C07G 7/00; C07C 103/52; A61K 37/36

[52] U.S. Cl. ............................. 424/177; 260/112 R; 424/95

[58] Field of Search ............. 260/112 R; 424/95, 177

[56] References Cited

U.S. PATENT DOCUMENTS 4,195,017 3/1980 Bogoch ........................... 260/112 R

OTHER PUBLICATIONS

Trowell et al., 3 Exp. Biol. 16, 60–70 (1939).
Hoffman, Growth, 4, 361–376 (1940).
Gospodarowicz et al., 3rd International Symposium on Growth Hormones, Sep. 1976.
Gospodarowicz et al. J. Biol. Chem., 253, 3736–3743 (1978).
Gospodarowicz et al., Ad. in Metabolic Disorders, vol. 8, 301–335 (1975).
Westall et al., Proc. Natl. Acad. Sci. USA, 75, 4675–4678 (1978).
Thomas et al., J. Biol. Chem. 255, 5517–5520 (1980).
Lemmon et al. J. Cell Biol. 95, 162–169 (1982).

*Primary Examiner*—Howard E. Schain
*Attorney, Agent, or Firm*—William H. Nicholson; Mario A. Monaco

[57] ABSTRACT

Acidic brain fibroblast growth factor isolated from bovine brain, is purified by a particular combination of protein purification techniques. The product is useful in the promotion of cell division (mitogenesis) such as in the promotion of wound healing.

8 Claims, No Drawings

PURIFICATION AND CHARACTERIZATION OF A PROTEIN FIBROBLAST GROWTH FACTOR

SUMMARY OF THE INVENTION

This invention is concerned with a growth factor useful in promoting wound healing isolated from bovine brain. The acidic brain fibroblast growth factor is purified a minimum of 35,000-fold to apparent homogeneity by a combination of differential salt precipitation, ion exchange, gel filtration, isoelectric focusing and hydrophobic chromatography on a C4 reverse phase HPLC column. Two microheterogenous forms of the molecule are obtained with apparent molecular masses of 16,600 and 16,800 daltons.

BACKGROUND OF THE INVENTION

Mitogenic activity for fibroblasts was recognized in brain extracts over 40 years ago by Trowell et al., (1939) J. Exp. Biol., 16, 60–70 and Hoffman, (1940) Growth, 4, 361–376. The first claim of purification to homogeneity of a brain-derived growth factor was made by Gospodarowicz, et al., (1976) Third International Symposium on Growth Hormone and Related Peptides, Sept. 17–20 (1975) Milan, Italy, Excerpta Medica/Elsevier, New York, pp. 141–165 and (1978) J. Biol. Chem. 253, 3736–3743., who described a variety of activities and target cells of the mitogen, Gospodarowicz, et al., (1975) in Adv. in Metabolic Disorders, eds., Luft, R. & Hall, K. (Academic Press, New York) Vol. 8, 301–335. After an approximately 1000-fold purification from a crude bovine brain homogenate the active protein, fibroblast growtn factor (FGF), was reported to be a family of 3 proteolytic fragments of myelin basic protein, Westall, et al., (1978) Proc. Natl. Acad. Sci. USA 75, 4675–4678, a constituent of the myelin sheath surrounding many brain and peripheral neurons.

The identification of the mitogens as degradation products of myelin basic protein subsequently was disputed, Thomas, et al., (1980) J. Biol Chem. 255, 5517–5520 and Lemmon, et al., (1982) J. Cell Biol 95, 162–169, and the fragments of myelin basic protein were ultimately confirmed to be the major protein species in these preparations but were not the active mitogens.

Now, with this invention, there is provided a process for the 35,000-fold purification of acidic brain fibroblast growth factor and a characterization of the protein.

Also provided by this invention are pharmaceutical compositions comprising the novel growth factor as active ingredient, and a method of treating wounds of mammals including humans by the administration of the novel growth factor to patients in need of such treatment.

DETAILED DESCRIPTION OF THE INVENTION

The novel growth factor of this invention is an acidic brain fibroblast growth factor in substantially pure form which exists as two microheterogeneous forms with masses of 16,600 and 16,800 daltons with an amino acid composition as shown in Table I.

TABLE I

| Amino Acid | Units |
|---|---|
| Aspartic Acid } Asparagine | 14 |
| Threonine | 9 |
| Serine | 10 |
| Glutamic Acid } Glutamine | 16 |
| Proline | 7 |
| Glycine | 14 |
| Alanine | 5 |
| Cysteine | 4 |
| Valine | 5 |
| Methionine | 1 |
| Isoleucine | 6 |
| Leucine | 19 |
| Tyrosine | 7 |
| Phenylalanine | 7 |
| Histidine | 5 |
| Lysine | 13 |
| Arginine | 6 |
| Tryptophan | 1 |

One unit of mitogenic activity for BALB/c 3T3 cells, the amount of pure protein required for half-maximal stimulation of synthesis of DNA, corresponds to 40 pg/ml of growth factor.

Although the acidic brain fibroblast growth factor of this invention is described as being isolated from bovine brain, the same or substantially similar growth factors may be isolated from other mammalian brain, including human brain.

The novel process of this invention for isolation of the acidic brain fibroblast growth factor from the above mammalian tissue comprises the sequence of steps of:

(1) extraction and differential salt precipitation from the source tissue;
(2) ion exchange;
(3) gel filtration;
(4) ion exchange;
(5) isoelectric focusing; and
(6) hydrophobic reverse phase chromatography.

The extraction and differential salt precipitation is accomplished by sequential treatments with 0.15 M ammonium sulfate at pH 4.5; 1.52 M ammonium sulfate at pH 6.75; and 3.41 M ammonium sulfate at pH 6.75 followed by dialysis and lyophilization of the high salt concentration precipitate.

The ion exchange step comprises batch adsorption on carboxymethyl-Sephadex (Pharmacia)resin at pH 6 followed by sequential elution with 0.1 M sodium phosphate buffer containing 0.15 M and 0.60 M sodium chloride followed by dialysis and lyophilization of the 0.60 M sodium chloride fraction.

The gel filtration step is performed on a Sephadex G-75 (Pharmacia) column by elution with 0.1 M ammonium bicarbonate, pH 8.5 followed by lyophilization of the pooled hightest activity fractions.

A second ion exchange step is performed on a carboxymethyl cellulose column being loaded in 0.1 M ammonium formate, pH 6.0 and eluted with 0.2 M and 0.6 M ammonium formate, pH 6.0, in sequence followed by lyophilization of the active pool.

Isoelectric focusing is performed in Ultrodex (LKB, Gaithersburg, MD).

Hydrophobic reverse phase high performance liquid chromatographic purification of the acidic mitogenic activity is achieved on Vydac C4 silica based HPLC column (The Separations Group, Hesperia, CA).

EXAMPLE

STEP 1: Extraction and Salt Precipitation

Bovine brains were obtained from a local slaughterhouse and transported on ice. Visible blood clots and the outer membrane of the meninges with their constituent blood vessels were removed. The brains were sliced into cubes approximately 2 cm on an edge, quick frozen in liquid $N_2$ and stored at $-70°$ C. Distilled water was used to make all solutions and pH values were adjusted versus standards at the temperature of use. All steps were performed at 4° C. unless otherwise noted.

Four kg of tissue (about 12 whole adult bovine brains) were thawed in 4 liters of 0.15 M $(NH_4)_2SO_4$, homogenized in a Waring blender and adjusted to pH 4.5 using 6N HCl while vigorously mixing with a 6 inch diameter propeller stirrer. After 1 hour the homogenate was centrifuged at 13,800×g for 40 minutes, the supernatant adjusted to pH 6.75 with 1 M NaOH and 200 g/liter of $(NH_4)_2SO_4$ (1.52 M) slowly added while stirring. After centrifugation at 13,800×g for 30 minutes, 250 g of $(NH_4)_2SO_4$ was added per liter of supernatant (3.41 M). The mixture was recentrifuged, the resulting pellet dissolved in 200 ml of water, dialyzed 18 hours in 6,000–8,000 $M_r$ cutoff bags (Spectrum Medical Industries, Los Angeles, Calif.) versus two 14 liter volumes of water and lyophilized.

STEP 2: Carboxymethyl-Sephadex Chromatography

Lyophilized protein from the salt precipitate of 16 kg of brain was dissolved in 900 ml of 0.05 M sodium phosphate, pH 6.0, the mixture readjusted to pH 6.0 with 1M NaOH and clarified by centrifugation at 23,300×g for 30 minutes. The supernatant was stirred for 15 minutes with 800 ml of hydrated Carboxymethyl-Sephadex C-50 (Pharmacia, Piscataway, N.J.) equilibrated with 0.1 M phosphate buffer, the unadsorbed protein sucked out on a coarse sintered glass filter, the resin washed with 3 liters of 0.1 M buffer and packed into a column of 8.3 cm diameter. The protein was sequentially eluted at 30 ml/min with 0.1 1M buffer containing 0.15 M and 0.60 M NaCl. The approximately 500 ml pool of the protein peak eluted by 0.6 M NaCl was dialyzed in 6,000–8,000 $M_r$ bags for 18 hours versus two 14 liter volumes of water and lyophilized.

STEP 3:

One-quarter of the lyophilized protein from the C-50 column was dissolved in 20 ml of 0.1 M ammonium bicarbonate, pH 8.5, clarified by a 15 minute centrifugation at 27,000×g and fractionated on a Sephadex G-75 (Pharmacia) (40–120 μm particle size) column (5×90 cm) at a flow rate of 74 ml/hr, 17.5 ml fractions being collected. The highest activity fractions (about 875 to 1050 ml. of eluate) were pooled and lyophilized.

STEP 4: Carboxymethyl Cellulose Chromatography

Protein from the Sephadex G-75 column was dissolved in 10 ml of 0.1 M ammonium formate, pH 6.0, the pH readjusted to pH 6.0 with 0.1 M formic acid, clarified by centrifugation at 27,000×g for 15 minutes and the supernatant loaded on a CM52 carboxymethyl cellulose (Whatman, Clifton, N.J.) column (1.5×6.5 cm). The protein was eluted at 60 ml/hr with 0.2 M followed by elution of the growth factor with 0.6 M ammonium formate, pH 6.0. The active pool was lyophilized directly.

Step 5: Isoelectric Focusing

Protein samples were isoelectric focused in Ultrodex (LKB, Gaithersburg, Maryland) using a modified LKB Multiphor flatbed focusing plate with miniaturized focusing lanes. Isoelectric focusing was typically performed on a plate containing 3 lanes of 0.5×10 cm, each with 75 mg of Ultrodex in 1.9 ml of water containing 126 μl of pH 3–10 Pharmalyte (Pharmacia) and 47 μl of pH 9–11 Ampholine (LKB). The liquid was evaporated 32% by weight. Either the FGF sample or 1 mg each of cytochrome c and hemoglobin (Sigma, St. Louis, Mo.) was loaded in 100 μl of the above diluted ampholyte solution. The pH gradient reached equilibrium as monitored by the stability of the current, the positions of the cytochrome c and hemoglobin standards and the final pH profile. The gel was divided into ten 1 cm slices and each segment eluted by 3 sequential 5 minute centrifugations with 333 μl of 0.6 M NaCl at 200×g in a MF-1 microfiltration tube containing a 1 μm pore size regenerated cellulose RC-60 filter (Bioanalytic Systems Inc., West Lafayette, Indiana). The pH of each 1 ml eluate was measured versus 0°–5° C. standards.

Step 5: Reverse Phase HPLC Chromatography

Final purification was achieved on a Vydac $C_4$ silica based HPLC column (4.6×50 mm) (The Separations Group, Hesperia, Calif.) equilibrated in a 10 mM trifluoroacetic acid solution that was previously passed through a $C_{18}$ preparative reverse phase HPLC column to remove UV absorbing contaminants. The mitogenically active acidic (pH $\simeq$5–7) fractions eluted from the focusing resin were injected directly on the column. The column was developed with a 0–67% acetonitrile gradient, the active protein being eluted at approximately 30–35% acetonitrile.

Mitogenic Assay

BALB/c 3T3 A31 fibroblasts (American Type Culture Collection, Rockville, Maryland) were plated at $2\times10^4$ cells per 35 mm diameter well as described by Thomas, et al., (1980) *J. Biol. Chem.*, 255, 5517–5520 and incubated in 7% $CO_2$ (pH 7.35±0.05). The cells became fully quiescent by replacing the media with 0.5% heat inactivated calf serum 6 and again 24 hours later. At 55 hours after plating, test samples 1.1 μg of and dexamethasone were added, at 70 hours each well was supplemented with 2 μCi of [methyl-$^3$H]-thymidine (20 Ci/mmole, New England Nuclear, Boston, Massachusetts) and 3 μg of unlabeled thymidine (Sigma), and at 95 hours the cells were processed for determination of incorporated radiolabel as documented (Thomas, et al., *J. Biol. Chem.*, 255, 5517–5570). Each dose-response point was the average of triplicate determinations. The amount of mitogenic activity in each chromatographic pool was determined from dose-response curves established from 4 or more measurements at 10-fold increments of protein sample concentration. This gave substantially more accurate and reproducible determinations of mitogenic activity than commonly used single concentration assays. One unit of mitogenic activity is defined as the amount of protein needed to elicit a ½ maximal rise in activity from which the total number of activity units per pool was calculated.

Determination of Molecular Mass

Polyacrylamide gel electrophoresis of pure growth factor in the presence of a denaturant (sodium dodecyl sulfate), with or without a reductant (B-mercaptoethanol) revealed a pair of very close bands at 16,600 and 16,800 daltons. Amino acid analysis demonstrated that these were microheterogeneous forms of the same protein.

Amino Acid Analysis

Protein samples eluted from the HPLC column were evaporated to dryness and hydrolyzed in 6N HCl (Ultrex, Baker Chemical Co., Phillipsburg, N.J.) containing 2% phenol for 24, 48 and 72 hours. Cysteine content was determined as cysteic acid after performic acid oxidation Moore, (1963) *J. Biol Chem.*, 238, 235-237. Tryptophan was measured after hydrolysis in 4N N-methanesulfonic acid (Pierce, Rockford, Ill.) for 24 hours Simpson, et al., (1976) *J Biol. Chem.*, 251, 1936-1940. All analyses were performed on a Beckman 121 MB amino acid analyzer.

Employing the biochemical procedures and analytical techniques described supra, the stepwise purification summarized in Table II is accomplished. Overall, there was a purification factor of 35,000.

TABLE II

Purification of Acidic Brain FGF[a]

| Purification Step | Protein Recovery (mg) | Activity Recovery (units) | Activity Recovery (%)[b] | Sp. Activity (units/mg) | Purification Factor[b] |
|---|---|---|---|---|---|
| Brain homogenate | $1.1 \times 10^{5c}$ | $7.9 \times 10^7$ | 100 | $7.2 \times 10^2$ | 1.0 |
| Salt fractionated | $1.8 \times 10^{4c}$ | $5.2 \times 10^7$ | 66 | $2.9 \times 10^3$ | 4.0 |
| Sephadex C-50 | $5.9 \times 10^{2d}$ | $2.5 \times 10^7$ | 32 | $4.2 \times 10^4$ | 58.0 |
| Sephadex G-75 | $2.1 \times 10^{2d}$ | $1.2 \times 10^7$ | 15 | $5.7 \times 10^4$ | 79.0 |
| CM52 | $54^e$ | $1.0 \times 10^7$ | 13 | $1.85 \times 10^5$ | $2.6 \times 10^2$ |
| Isoelectric focusing | —[f] | $3.6 \times 10^6$ | 4.6 | — | — |
| C4HPLC | $0.144^g$ | $3.2 \times 10^6$ | 4.1 | $2.5 \times 10^7$ | $3.5 \times 10^4$ |

[a]Values based on 4 kg of bovine brain.
[b]Except for the value for the homogenate, these are minimum values that are estimated assuming that all of the initial mitogenic activity is acidic brain FGF.
[c]Protein estimated by 260/280 ratio method (Data for Biochemical Research, 2nd ed. (1969) eds. Dawson, R. M. C., Elliott, D. C., Elliott, W. H. and Jones, K. M. (Oxford Univ. Press, London) pp. 626-627).
[d]Protein estimated using $E_{280}^{1\%} = 10$.
[e]Protein estimated using $E_{280}^{1\%} = 7.9$.
[f]Protein not quantitated.
[g]Protein quantitated by amino acid analysis.

Another embodiment of this invention is a method of promoting the healing of wounds by application of the novel peptide of this invention to the wound area either topically or subcutaneously near the edge of the wound in an amount of about 0.1 to 100 µg/cm² of surface for topical application.

For application, various pharmaceutical formulations are useful such as ointments, pastes, solutions, gels, solid water soluble polymers such as hydroxypropyl cellulose in which the active ingredient is incorporated in amounts of about 10 µg/ml.

What is claimed is:

1. An acidic brain fibroblast growth factor in substantially pure form with molecular mass of 16,600 or 16,800 daltons and an amino acid composition of:

| Amino Acid | Units |
|---|---|
| Aspartic Acid Asparagine | 14 |
| Threonine | 9 |
| Serine | 10 |
| Glutamic Acid Glutamine | 16 |
| Proline | 7 |
| Glycine | 14 |
| Alanine | 5 |
| Cysteine | 4 |

-continued

| Amino Acid | Units |
|---|---|
| Valine | 5 |
| Methionine | 1 |
| Isoleucine | 6 |
| Leucine | 19 |
| Tyrosine | 7 |
| Phenylalanine | 7 |
| Histidine | 5 |
| Lysine | 13 |
| Arginine | 6 |
| Tryptophan | 1 |

2. The acidic brain fibroblast growth factor of claim 1, isolated from bovine brain.

3. A process for the isolation of acidic brain fibroblast growth factor in substantially pure form which comprises the sequence of steps of:
(1) extraction and differential salt precipitation from the source tissue;
(2) ion exchange;
(3) gel filtration;
(4) ion exchange;
(5) isoelectric focusing;
(6) hydrophobic reverse phase chromatography.

4. The process of claim 3 for the isolation from bovine brain.

5. The process of claim 3 wherein:
(1) The extraction and differential salt precipitation is accomplished by sequential treatments with 0.15 M ammonium sulfate at pH 4.5; 1.52 M ammonium sulfate at pH 6.75; and 3.41 M ammonium sulfate at pH 6.75 followed by dialysis and lyophilization of the high salt precipitate;
(2) the ion exchange comprises batch adsorption on carboxymethyl-Sephadex (Pharmacia) resin at pH 6 followed by sequential elution with 0.1 M sodium phosphate buffer containing 0.15 M and 0.60 M sodium chloride followed by dialysis and lyophilization of the 0.60 M sodium chloride fraction,
(3) gel filtration on a Sephadex G-75 (Pharmacia) column by elution with 0.1 M ammonium bicarbonate, pH 8.5 followed by lyophilization of the pooled high activity fractions;
(4) ion exchange on a carboxymethyl cellulose column loaded in 0.1 M ammonium formate, pH 6.0 and eluted with 0.2 M and 0.6 M ammonium formate, pH 6.0, in sequence followed by lyophilization of the active pool;

(5) isoelectric focusing is in Ultrodex (LKB, Gaithersburg, Md.); and
(6) hydrophobic reverse phase high performance liquid chromatographic purification of the acidic mitogen is on Vydac $C_4$ silica based HPLC column (The Separations Group, Hesperia, Calif.).

6. The process of claim 5 for the isolation from bovine brain.

7. A pharmaceutical growth promoting composition comprising a pharmaceutical carrier and an effective growth promoting amount of the fibroblast growth factor of claim 1.

8. A method of promoting wound healing which comprises the administration to a patient in need of such treatment of an effective growth promoting amount of the fibroblast growth factor of claim 1.

* * * * *